US011237525B2

(12) United States Patent
Pi

(10) Patent No.: US 11,237,525 B2
(45) Date of Patent: Feb. 1, 2022

(54) SMART WATCH

(71) Applicant: SHENZHEN GOODIX TECHNOLOGY CO., LTD., Shenzhen (CN)

(72) Inventor: Bo Pi, Carlsbad San Diego, CA (US)

(73) Assignee: SHENZHEN GOODIX TECHNOLOGY CO., LTD., Shenzhen (CN)

(*) Notice: Subject to any disclaimer, the term of this patent is extended or adjusted under 35 U.S.C. 154(b) by 438 days.

(21) Appl. No.: 14/793,576

(22) Filed: Jul. 7, 2015

(65) Prior Publication Data
US 2016/0004224 A1 Jan. 7, 2016

Related U.S. Application Data

(60) Provisional application No. 62/021,657, filed on Jul. 7, 2014, provisional application No. 62/034,723, filed on Aug. 7, 2014.

(51) Int. Cl.
A61B 5/00 (2006.01)
G04G 21/02 (2010.01)
(Continued)

(52) U.S. Cl.
CPC ......... G04G 21/025 (2013.01); A61B 5/0002 (2013.01); A61B 5/0205 (2013.01);
(Continued)

(58) Field of Classification Search
CPC ............ G04G 21/025; A61B 5/02438
See application file for complete search history.

(56) References Cited

U.S. PATENT DOCUMENTS 7,751,595 B2  7/2010 Russo
8,725,842 B1  5/2014 Al-Nasser
(Continued)

FOREIGN PATENT DOCUMENTS

CN 1011061481 A 10/2007
CN  101902956 A 12/2010
(Continued)

OTHER PUBLICATIONS

International Search Report and Written Opinion dated Dec. 7, 2015 for International Application No. PCT/US2015/039433, filed on Jul. 7, 2015 (11 pages).
(Continued)

Primary Examiner — John R Downey
(74) Attorney, Agent, or Firm — Perkins Coie LLP

(57) ABSTRACT

A smart watch described in this document includes hardware and software necessary to obtain motion and sensor data from a user wearing the smart watch. The described smart watch can continuously collect sensor data from the user and combine the sensor data from multiple sensors to enhance the accuracy of the sensor data analysis and provide relevant feedback information to the user. In addition, the described smart watch is capable of pairing with an external personal portable device, such as a smartphone or tablet to correlate the collected sensor data with activities performed by the user on the paired device. The smart device can also transmit data to a cloud server to collect sensor data and correlation analysis data for further analysis and provide statistical analysis of the collected sensor data and correlation analysis data.

26 Claims, 6 Drawing Sheets

(51) Int. Cl.
*G04G 21/04* (2013.01)
*A61B 5/024* (2006.01)
*A61B 5/0205* (2006.01)
*A61B 5/11* (2006.01)
*A61B 5/021* (2006.01)

(52) U.S. Cl.
CPC ............ *A61B 5/02438* (2013.01); *A61B 5/11* (2013.01); *A61B 5/681* (2013.01); *A61B 5/7475* (2013.01); *G04G 21/04* (2013.01); *A61B 5/021* (2013.01)

(56) References Cited

U.S. PATENT DOCUMENTS

| | | | |
|---|---|---|---|
| 2004/0171956 A1* | 9/2004 | Babashan | A61B 5/02438 600/509 |
| 2008/0214902 A1* | 9/2008 | Lee | A61B 5/165 600/301 |
| 2009/0075781 A1* | 3/2009 | Schwarzberg | G16H 40/67 482/8 |
| 2009/0131764 A1* | 5/2009 | Lee | H04N 21/42201 600/301 |
| 2011/0085780 A1* | 4/2011 | Fukuyori | G06F 16/70 386/241 |
| 2011/0160550 A1* | 6/2011 | Hwang | G06F 16/4387 600/301 |
| 2011/0263331 A1 | 10/2011 | Koski et al. | |
| 2012/0083705 A1* | 4/2012 | Yuen | A61B 5/743 600/508 |
| 2013/0194066 A1* | 8/2013 | Rahman | G05B 1/01 340/5.51 |
| 2013/0209972 A1* | 8/2013 | Carter | G16H 20/30 434/127 |
| 2014/0073486 A1* | 3/2014 | Ahmed | A61B 5/02438 482/9 |
| 2014/0127996 A1* | 5/2014 | Park | H04W 4/027 455/41.1 |
| 2014/0143064 A1 | 5/2014 | Tran | |
| 2014/0275854 A1* | 9/2014 | Venkatraman | A61B 5/721 600/301 |
| 2015/0093729 A1* | 4/2015 | Plans | A61B 5/0476 434/236 |
| 2015/0118665 A1* | 4/2015 | Armstrong | G06Q 10/101 434/236 |
| 2015/0286813 A1* | 10/2015 | Jakobsson | G06F 21/35 726/9 |
| 2016/0179197 A1 | 6/2016 | Qian et al. | |
| 2016/0224816 A1 | 8/2016 | Smith et al. | |

FOREIGN PATENT DOCUMENTS

| | | |
|---|---|---|
| CN | 103124971 A | 5/2013 |
| CN | 103605504 A | 2/2014 |
| CN | 103870220 A | 6/2014 |
| CN | 103876714 A | 6/2014 |

OTHER PUBLICATIONS

Chinese Office Action from Chinese Patent Application No. 201580007723.7 dated Jun. 25, 2018 (6 pages).
Chinese Office Action from Chinese Patent Application No. 201580007723.7 dated Mar. 1, 2019. (7 Pages).
Indian Examination Report from Indian Application No. 201617037656 dated Sep. 30, 2019.

* cited by examiner

SMART WATCH

CROSS REFERENCE TO RELATED APPLICATIONS

This patent document claims the benefit of priority of U.S. Provisional Patent Application No. 62/021,657, filed on Jul. 7, 2014, and U.S. Provisional Patent Application No. 62/034,723, filed on Aug. 7, 2014. The entire contents of the before-mentioned patent applications are incorporated by reference as part of the disclosure of this document.

BACKGROUND

This application relates to devices, techniques and systems for collecting motion and biometric sensor data from a user is described.

SUMMARY

Techniques, systems and apparatus are described for implementing a smart watch that provides continuous sensing and combined sensor data from a combination of sensors, such as a motion sensor and a biometric sensor. The smart watch as described can correlate sensor data from multiple sensors and correlate the combined sensor data with an activity performed on a paired device. The collected combined sensor data and correlated data can be uploaded to a cloud server to provide relevant use feedback, perform statistical analysis and create cloud based services (e.g. sensor ratings) based on the collected combined sensor data.

In one aspect, a smart watch includes at least one motion sensor to sense motion data; at least one biometric sensor to sense biometric data; a microcontroller to control the motion and biometric sensors; a real-time clock to maintain time; a wireless radio to pair with an external device; and a display module. The microcontroller can analyze sensor data from two or more of the at least one motion sensor and biometric sensor to switch between multiple modes of operation.

The smart watch can be implemented in various ways to include one or more of the following features. For example, the microcontroller can analyze a combined sensor data from two or more of the at least one motion sensor and biometric sensor to identify a user's activity. The two or more of the at least one motion sensor and biometric sensor can include a 3-D accelerometer and a heart rate sensor respectively. The identified user activity can include a form of exercise. The microcontroller can analyze sensor data from the heart rate sensor to estimate total calories burned during the identified activity. The microcontroller can identify a medically significant event based on the combined sensor data from the 3-D accelerometer and the heart rate sensor. The wireless radio can include a Bluetooth low energy (BLE) radio. The BLE radio can pair with the external device comprising a smart phone. The microcontroller can sync time with the paired smart phone. The BLE radio can pair with the external device comprising a smart phone. The microcontroller can correlate sensor data from two or more of the at least one motion sensor and biometric sensor with an activity performed on the smart phone. The activity performed on the smart phone can include paying for a media file. The activity performed on the smart phone can include using an application. The activity performed on the smart phone can include consuming content on a web browser. The smart watch can include memory for storing an application program interface (API). The API can collect sensor data from two or more of the at least one motion sensor and biometric sensor during the activity and transmit the collected data to a cloud server. The BLE radio can pair with the external device comprising a smart phone. The microcontroller can correlate sensor data from two or more of the at least one motion sensor and biometric sensor with actual events stored on a calendar or schedule application of the smart phone. The at least one motion sensor and biometric sensor can continuously collect sensor data. The smart watch can include one or more touch sensors for receiving user input. The one or more touch sensors can be integrated into the display module. The one or more touch sensors can be located at one or more surfaces separate from the display module. The one or more surfaces separate from the display module can include a surface around or next to the display module. The one or more surfaces separate from the display module can include a surface of a wrist band. The display module can include a display device selected from the following: an organic light emitting diode (OLED) display, an E-ink display, a liquid crystal display (LCD), and a simply multiple LED display. The display module can display text and graphic information. The microcontroller can analyze a combined sensor data from two or more of the at least one motion sensor and biometric sensor to identify a user's activity. The smart watch can include a data storage device configured to operate in concert with the microcontroller to store sensor data from the one or more motion or biometric sensors when operating independent of and not in communication with an external device. The microcontroller and the wireless radio in combination can transfer sensor data to the external device or to a cloud server when the smart watch is within a wireless communication range with the external device. The smart watch can include a fingerprint sensor configured to attempt to authenticate a user as a valid user of the smart watch. The fingerprint sensor can attempt to authenticate the user as a valid user of the smart watch by comparing matching sensed fingerprint print data with stored fingerprint profile of the valid user of the smart watch. The one or more motion sensors or the one or more biometric sensors can determine whether the user is wearing the smart watch.

In another aspect, a method performed by a smart watch includes sensing at least one motion data; sensing at least one biometric data; analyzing, by a controller, the at least one motion data and the at least one biometric data; and responsive to the analysis, switching between multiple modes of operation of the smart watch.

The method can be performed to include one or more of the following features. For example, the method can include analyzing a combination of the at least one motion data and the at least one biometric data to identify a user's activity. Identifying a user's activity can include identifying a total calories burned during the identified activity. The method can include correlating the combination of the at least one motion data and the at least one biometric data to the identified user activity.

In another aspect, a cloud server includes a computing system configured to receive a combined sensor data collected from at least a motion sensor and a biometric sensor transmitted from a smart watch; and analyze the received combined sensor data to generate a rating system for the combined sensor data correlated to an activity performed by a user of the smart watch. The computing system can receive the combined sensor data from multiple smartwatches. The computing system can correlate the combine sensor data with a given application or content being consumed on the smart watch. The computing system can correlate the combined sensor data to the application or content being consumed on the smartwatch to identify a reaction to the application or content. The computing system can correlate the combined sensor data to the activity performed by as user of the smartwatch to identify a reaction to the activity.

BRIEF DESCRIPTION OF THE DRAWINGS

Like reference symbols and designations in the various drawings indicate like elements.

DETAILED DESCRIPTION

A smart watch described in this document includes hardware and software necessary to obtain motion and sensor data from a user wearing the smart watch. The described smart watch can continuously collect sensor data from the user and combine the sensor data from multiple sensors to enhance the accuracy of the sensor data analysis and provide relevant feedback information to the user. In addition, the described smart watch is capable of pairing with an external personal portable device, such as a smartphone or tablet to correlate the collected sensor data with activities performed by the user on the paired device. The smart watch device can also transmit data to a cloud server to collect sensor data and correlation analysis data for further analysis and provide statistical analysis of the collected sensor data and correlation analysis data. The smart watch device can also store the sensor data when it is separated from paired devices, and the smart watch device can transfer the stored sensor data to paired devices and to the cloud server when it comes in a wireless communication range (e.g., Bluetooth, low energy Bluetooth, 60 GHz, WiFi direct, etc.) of the paired devices. Thus, the smart watch device can include a standalone mode to fully operate including collection, storing and exchanging sensor data independent from the paired device.

The smart watch can include a correlation module to perform "cross correlation" between sensed measurements on the smart watch and "other off-watch" items in the cloud or on the other wireless computing device. The cross correlation between the watch and off watch items can include personal data mining. Examples of correlated data types include: calendar, email/phone communications, location, social media data, online purchasing/browsing (e.g., YouTube)

Also, the smart watch can combine sensor data from multiple motion and biometric data to more accurate track health related activities (e g., running, swimming, walking, etc.) to not only measure the extent of the user's motion but also the intensity of the user's motions during the activity. Biometric sensor data can couple with motion sensor data to identify activities that burn more calories, for example.

Similar to the health tracking application, the combined sensing of the motion and biometric sensors can be used to identify medically significant events, trigger sending of automated messages or warnings associated with the identified medically significant events, and take any appropriate actions.

Described below are various features of the described techniques, apparatus and systems and associated examples.

Connected Smart Watch: Continuous Combined Sensing

Figure 1A:
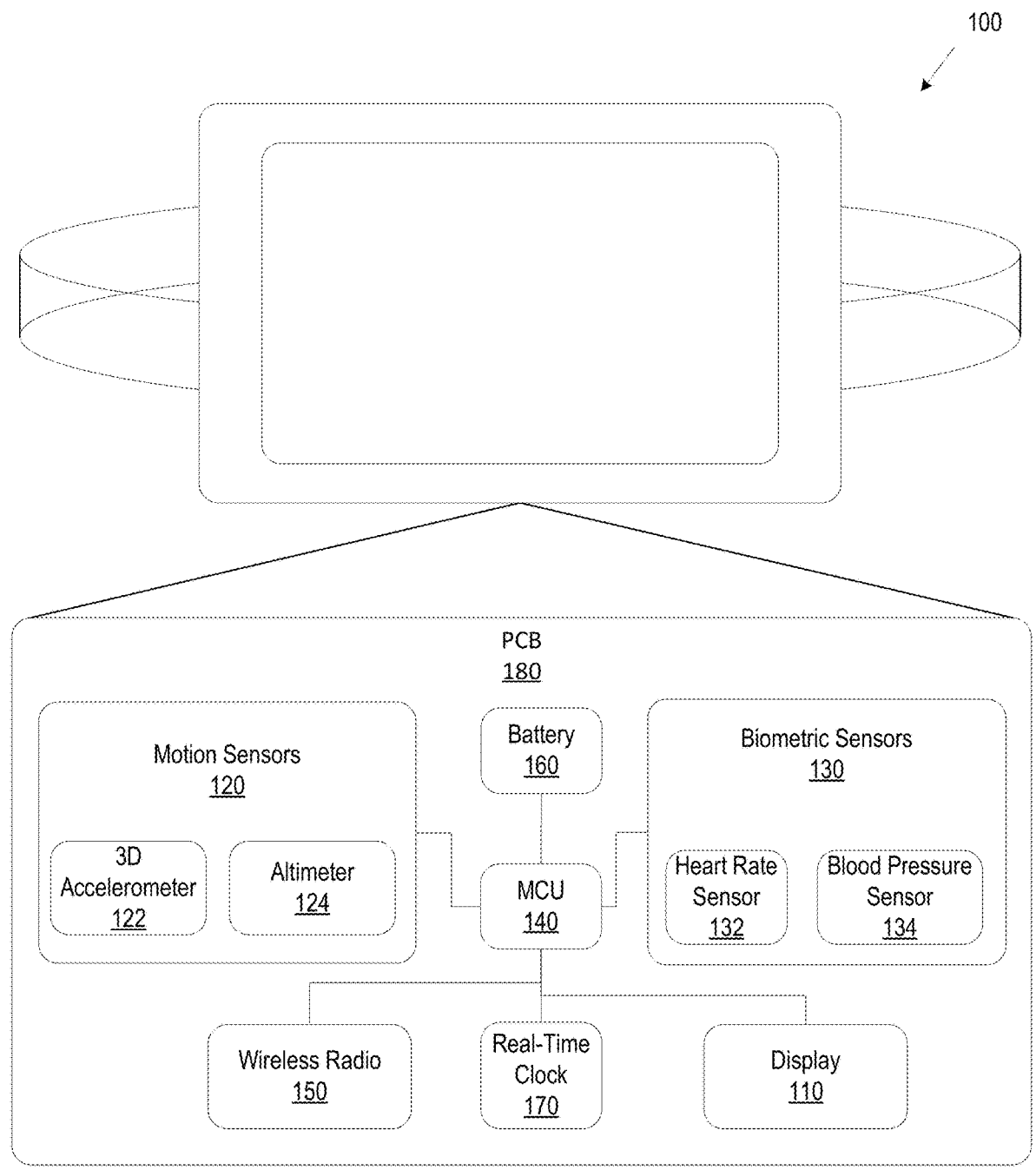
FIG. 1A is a block diagram showing an exemplary smart watch.

FIG. 1 shows an exemplary smart watch 100 for using a combination of sensors to continuously collect data associated with a user wearing the smart watch 100. A smart watch 100 includes a display module 110 for displaying information to the user. The display module 110 can display text and graphic information on the face of the smart watch, and can be implemented using an organic light emitting diode (OLED) display or E-ink display, LCD or simply multiple LEDs for display information.

The display module 110 can optionally include an integrated touch sensor for receiving touch input from a user wearing the smart watch 100. When included with the display module, the touch sensor on the display can be implemented as an ultra-low power touch sensor that can be always turned on or active to detect touch signals. The touch sensor can continuously touch gestures, such as slide cross, z shape slide, or single or double tap, etc. The touch sensor can also detect rotational slide on the edge of the smart watch, like the wheel slider on the edge of a regular watch, and is particular useful for a round shape watch face.

Figure 1B:
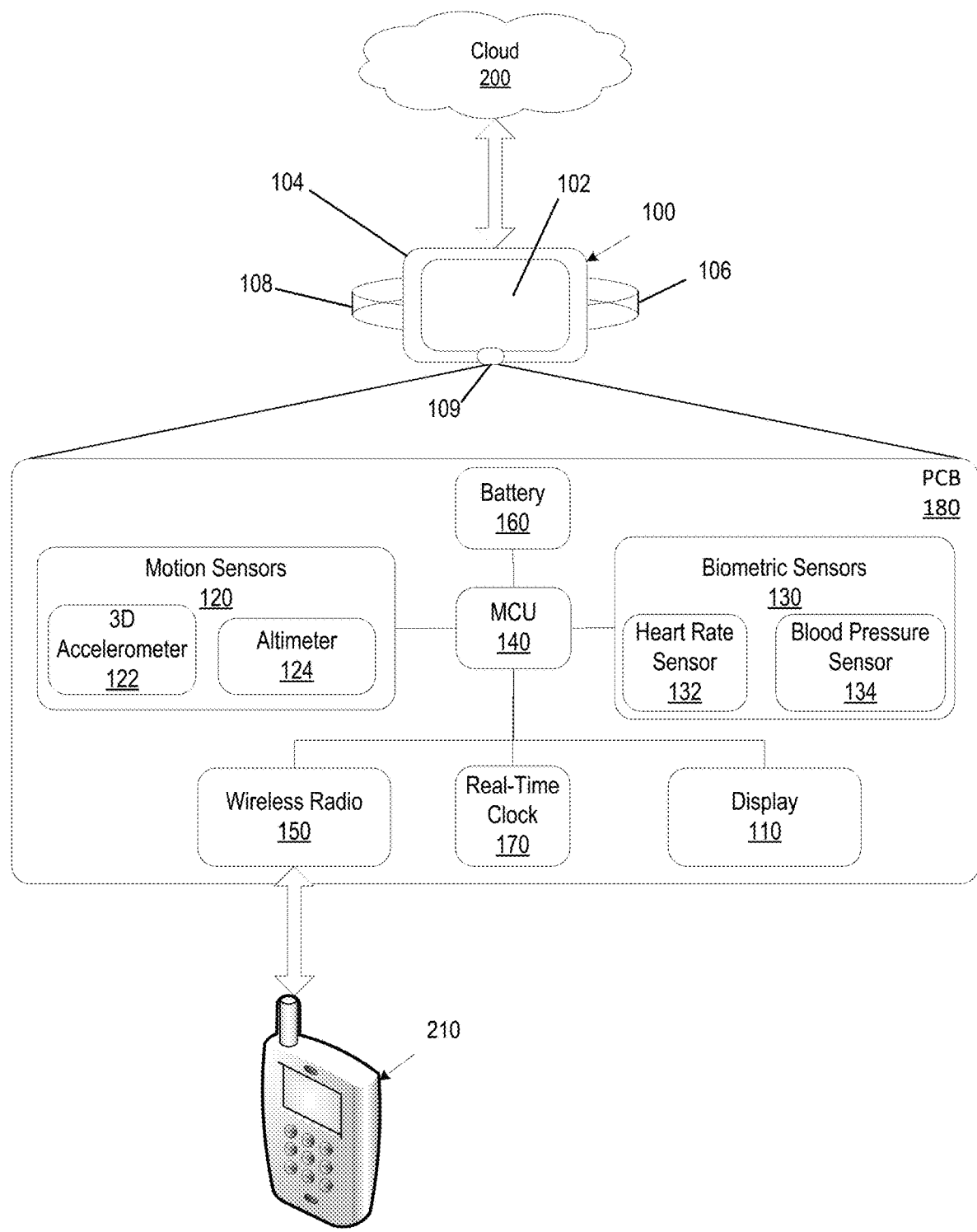
FIG. 1B is a block diagram showing an exemplary smart watch with optional touch sensors.

The optional touch sensor can be implemented at one or more surfaces independent from the display (i.e., not integrated with the display). For example, the optional touch sensor can be placed around or next to the display module but not integrated with the display. Also, the optional touch sensor can be located on the surface of a wrist band. FIG. 1B is a block diagram showing an exemplary smart watch 800 with optional touch sensors pairing with another device 210 or cloud server 200, or both. The optional touch sensor can be integrated with the display module 110 (see location 102), placed around or near but separate from the display module 110 (see location 104) or placed on the wrist strap (see location 106 and 108). The pairing of the smart watch 100 with an external device 200 is described further with respect to FIG. 2 below.

The smart watch 100 includes one or more motion sensors 120 such as a 3D accelerometer (e.g., G Sensor) 122 and an altimeter 124 for collecting movement and position data of the smart watch 100 worn on the user. The smart watch 100 includes one or more biometric sensors 130 such as a heart rate (HR) sensor 132 and a cuff-less blood pressure (BP) sensor 134 for collecting biometric data from the user wearing the smart watch 100 such as heart rate and blood pressure. In one example, the cuff-less BP sensor 134 can be implemented using two sensors positioned a predetermined distance apart to allow measurement of the blood flow rate between the know two points. The biometric sensors 130, 132 and 134 are located on the back of the smart watch 100 so at to be in contact with skin of the user wearing the smart watch 100. The ultra-low power HR sensor 132 can be an optical sensor located on the back of the smart watch, which makes direct contact with the user's skin, and always-on to continuously monitor the user's heart rate. A low power G sensor 122 on the smart watch 100 can stay powered on constantly (i.e., always-on) to monitor the smart watch's physical activities.

The motion and biometric sensors 120, 122, 124, 130, 132 and 134 are controlled by a microcontroller (MCU) 180 or a microprocessor to turn the motion and biometric sensors on/off, process collected sensor data and transmit the collected and processed sensor data through a wireless radio 190 such as a low energy Bluetooth (BLE) radio to an external device, network, cloud, etc. A battery 160 powers the smart watch 100 and is rechargeable. The rechargeable battery 160 can provide smart watch's normal operation for at least one full day. The smart watch 100 also includes a real-time clock 170 such as in a form of an integrated circuit to keep track of current time.

A printed circuit board (PCB) assembly 180 can be provided to integrate the MCU 140, real-time clock (RTC) 170, motion sensors 120 (including 3D accelerometer 122 and altimeter 124), biometric sensors 130 (including HR sensor 132 and BP sensor 134), wireless radio 150, such as BLE radio and battery 160.

Continuous Combined Sensing

The motion and biometric sensors 120, 122, 124, 130, 132 and 134 in the smart phone 100 are low-powered (i.e., consumes low power) and thus can be always on to obtain continuous sensor readings. Continuous sensor readings from the motion and biometric sensors 120, 122, 124, 130, 132 and 134 allow the smart watch 100 to obtain a historical sensor data and avoid missing an important motion and biometric event. In addition, the continuous sensor readings from a combination of sensors allow the smart watch 100 to make a more accurate analysis of the recorded sensor data, and predictions about the user wearing the smart phone 100 based on the analyzed sensor data. In addition, using sensor readings from a combination of sensors as a trigger to enable an event, operation or mode can prevent accidental triggering of an event, operation or mode by the user. Moreover, the continuous sensor readings from a combination of the motion and biometric sensors 120, 122, 124, 130, 132 and 134 allow the smart watch to customize the sensor data analysis and feedback for the user wearing the smart watch 100.

In addition to recording the collected sensor data, the smart watch 100 can perform various operations in response to input received from a combination of motion and biometric sensors. Specifically, the MCU 140 is in communication with the motion and biometric sensors 120, 122, 124, 130, 132 to perform various operations in response to the collected sensor data from a combination of the sensors. For example, responsive to sensor data received from a combination of the motion and biometric sensors, the MCU can change the operational mode of the smart watch 100. Examples of the sensor data received from a combination of sensors can include the following:

1. Combination of a signal from the G sensor and a signal from a heart rate sensor.
2. Combination of a signal on the G sensor that indicates a swing motion of user's arm for the user to see the smart watch and a signal from an optical sensor to confirm the user is maintaining eye-focus on the smart watch. In addition, an option to continuously keep the watch in a new mode or switch the smart watch to standby or standard mode in absence of positive optical sensor signal.

When the display module 110 is implemented to include an integrated touch sensor array, the following combinations of different sensor readings can be used to change between different operational modes.

1. Combination of a tap/touch on the touch screen and a signal from the G sensor.
2. Combination of a gesture on the touch sensor and a signal on the G sensor.
3. Combination of gestures on the touch sensor.
4. Combination of a double tap/touch on the touch sensor and a signal from the G sensor.
5. Combination of a signal on the G sensor that indicates a swing motion of user's arm for the user to see the smart watch and an option to continuously keep the watch in a new mode or switch the smart watch to standby or standard mode after a predetermined time duration without a touch sensor input.
6. Combination of another signature input from the G sensor, such as a simple shake of the smart watch (e.g., shake of user's arm) within a predetermined time duration after the detection of the first signature input from the G sensor, such as a single or double tap/touch on the connected/smart/correlated watch.

Also, the smart watch device can perform authentication functions. The smart watch device may include a finger print sensor to authenticate a valid user of the smart watch device. See FIG. 1B, reference number 109. During the first authentication attempt, the validity of the user can be authenticated using a fingerprint sensor profile match based on a fingerprint profile of a valid user of the smart watch device stored on the smart watch device or on the cloud or on the paired external device. In addition to the fingerprint sensor profile matching, the smart watch device can verify whether the authenticated valid user is still wearing the smart watch device by continuously or periodically monitoring biometric sensor data of the valid user currently wearing the smart watch. For example, heart beat sensor data can be monitored verify that the device is still being worn by the authenticated valid user of the smart watch. Using this secondary validation process, once the valid user of the smart watch device is authenticated for the first time (e.g., using fingerprint sensor profile matching), the smart watch device can remain in an authenticated mode until the device is taken off by the authenticated valid user of the smart watch device. In addition, the valid user of the smart watch device once authenticated and wearing the smart watch device can be pre-authorized to operate the paired external devices. In this manner, the authenticated valid user of the smart watch device can wear the smart watch device and operate the paired devices in authenticated mode automatically once within communication range (e.g., Bluetooth, low energy Bluetooth, WiFi direct, 60 GHz, etc.) of the paired external device. Thus, only the authenticated valid user of the smart watch device still wearing the smart watch device can operate the paired device in authenticated mode.

Based on the analysis of sensor data combinations described in the above examples, the smart watch 100 can switch to operate between multiple operational modes.

Figure 2:
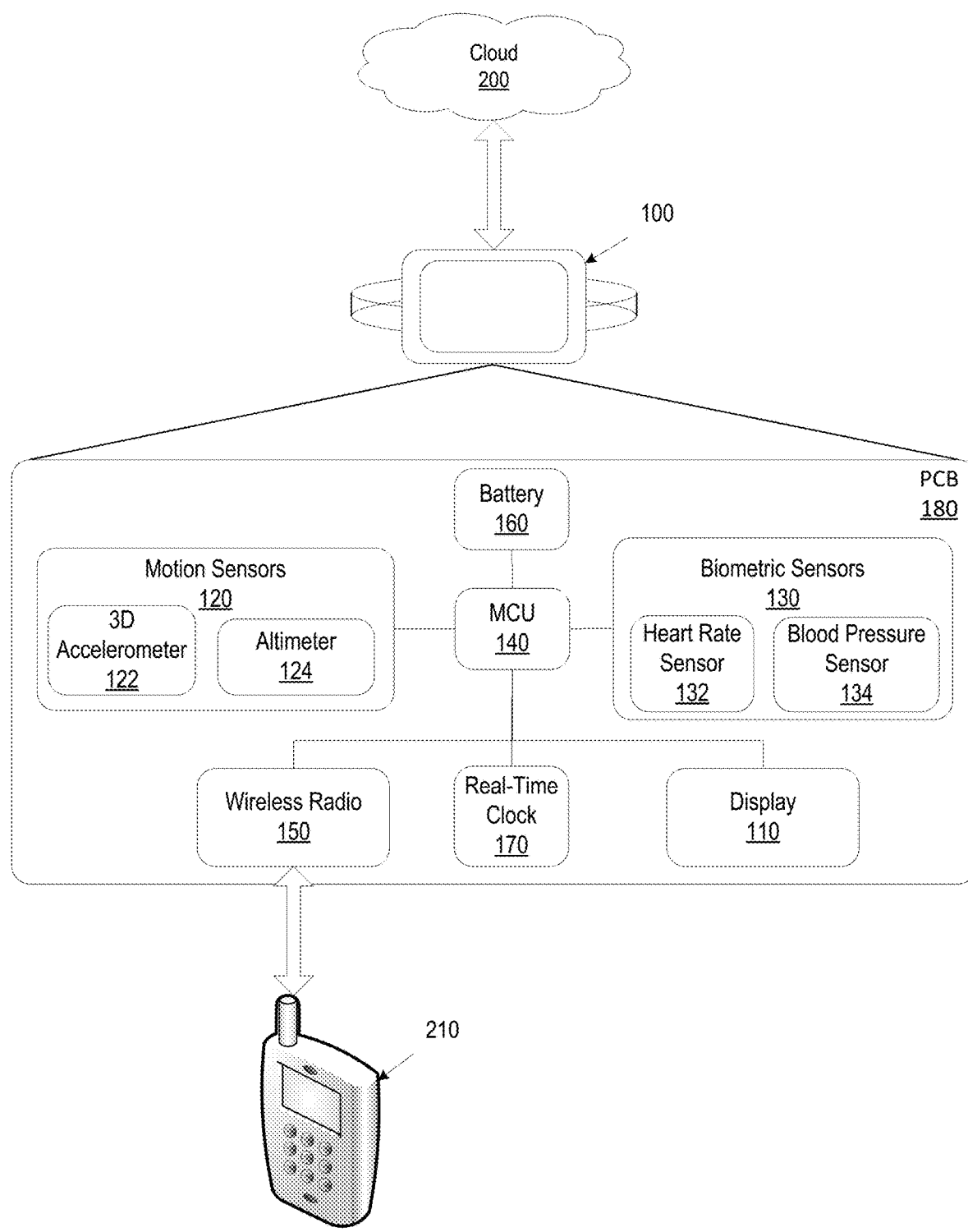
FIG. 2 is a block diagram showing an exemplary smart watch pairing with another device, cloud server, or both.

FIG. 2 is a block diagram showing an exemplary smart watch 100 pairing with another device 210, cloud server 200, or both.

Figure 3:
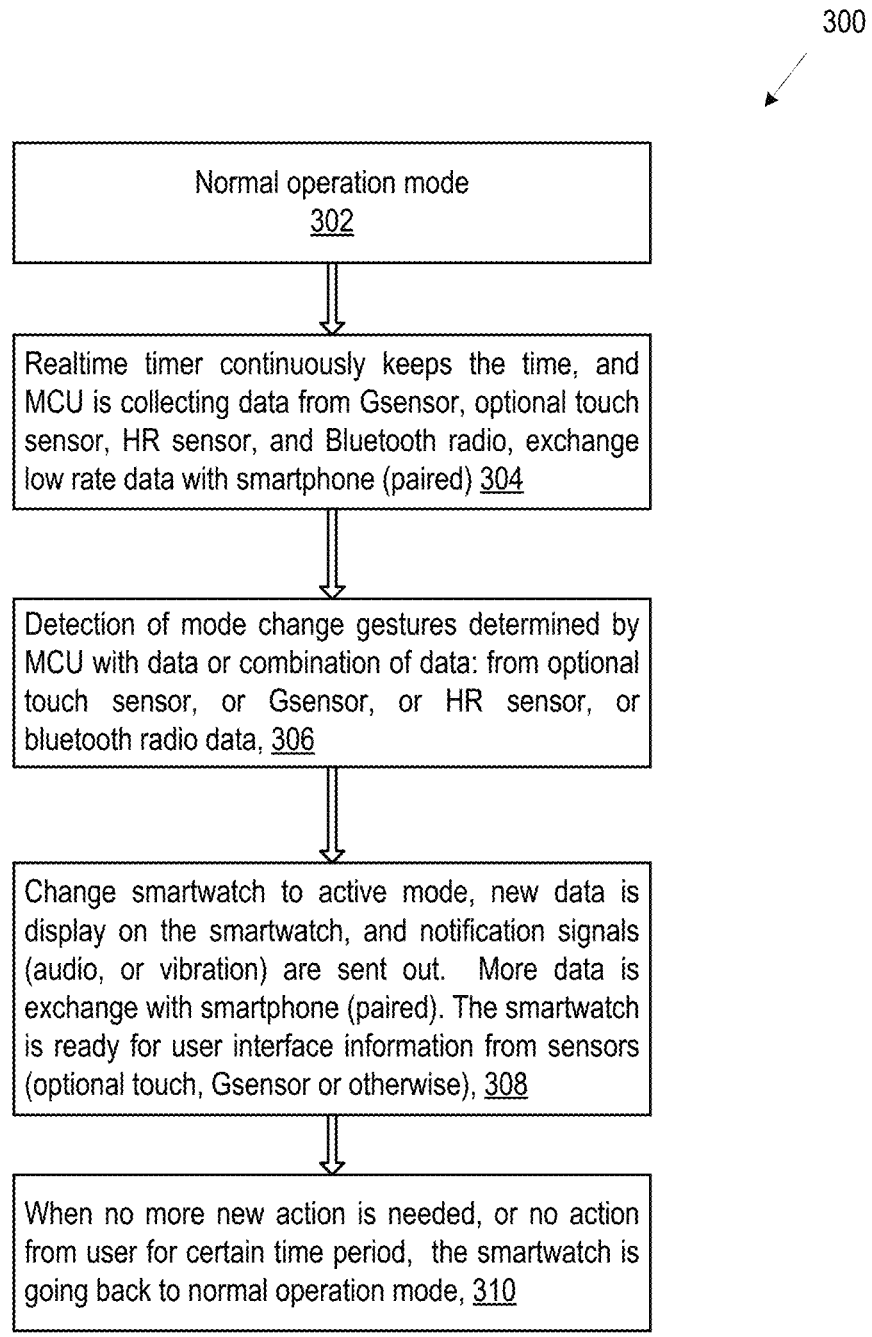
FIG. 3 is a flow diagram showing an exemplary process for switching between different modes of operation based on a combined sensing of multiple sensors.

FIG. 3 is a flow diagram showing an exemplary process 300 for switching between different modes of operation based on a combined sensing of multiple sensors. In standard normal mode, the smart watch 100 is operating as a standard time piece that displays the current time (302). During the standard mode, one or more of the motion and biometric sensors 120, 122, 124, 130, 132 can be in operation to collect motion or biometric sensor data in the background (304). The motion or biometric sensors in operation can continuously collect sensor data and make updates periodically (e.g., every second, every two second, every minute, etc.) (304). For example, a real-time timer can be used to continuously keep the time, and a microcontroller unit (MCU) is collecting data from sensors such as a Gsensor, optional touch sensor, or a HR sensor. In addition, the Bluetooth radio can exchange low rate data with a host device such as a smartphone when paired. The standard mode is a power saving mode because while the motion and biometric sensors are in operation and collecting sensor data, the smart watch is not actively taking actions or performing operations in response to the collected sensor data.

When operating in the standard mode (e.g., power saving mode), the smart watch can be setup to pair with a portable device such as a smart phone or a tablet computer to exchange information periodically or continuously through a wireless connectivity (e.g., Bluetooth radio) when a notification (e.g., text message, email or call) is sent by the smart phone to the smart watch 100.

Detection of a gesture that changes the mode can be determined by the MCU with data or combination of data from one or more of the sensors including the optional touch sensor, or Gsensor, or HR sensor, or Bluetooth radio data (306). Responsive to the detected gesture that indicates a change of the mode, the smartwatch can be changed to an active mode (308). In the active mode, new data is display on the smartwatch and notification signals (audio or vibration) can be output by the smartwatch. More data is exchange with a host device, such as the smartphone when paired. The smartwatch is ready for user interface information from sensors (optional touch, Gsensor or otherwise).

The smart watch 100 can change mode to display the information associated with the notification for a set period of time, and also send out an audio or vibration notice signal. During this period of time, an input collected by a combination of motion and biometric sensors can keep the smart watch 100 in full display operation mode, otherwise the smart watch 100 will turn back to power saving mode (the standard mode) to save power. For example, a user input can be collected by a biometric sensor and the G sensor to trigger the full display mode. When the display module 110 is implemented to include an integrated touch sensor array, user input can be collected using the sensor array in addition to the G sensor and the biometric sensor. Even after the triggering of the full display mode, the smart watch 100 can be set to return to the power saving standard mode if no additional input is received by the combination of motion and biometric sensor for a set period of time.

The MCU can use the RTC on the smart watch 100 to record the time of the collected data and any notifications received from the paired device (e.g., smart phone, tablet, etc.). In addition, the MCU can use the RTC to sync the time on the smart watch with the time on the paired device.

In another implementation, the MCU can analyze the G sensor data to determine whether or not the user is wearing the smart watch 100 on the user's arm. This can be based on the motions detected by the G sensor that indicates motions associated with the user's arm. If the MCU determines that the smart watch is being worn on the arm by user, the MCU can enable the HR sensor, and if the user's heart beat is detected continuously, the HR sensor will stay on unless the user actively turns off the HR sensor. In addition, if the HR sensor is already turned on (e.g., in an 'always on' operation), the HR sensor can determine whether the user is wearing the smart watch by the presence of the user's hear beat sensed. Thus, sensor data from one sensor can be used to turn on/off other sensors. In addition, sensor data from one or more sensors can be used to determine whether the user is wearing the smart watch 100 on the arm.

When no more new action is needed, or no action from user for certain time period, the smartwatch is going back to normal operation mode (310).

Continuous Combined Sensing for Health Monitoring Application

The MCU can analyze the HR sensor data continuously collected during a predetermined period of time (e.g., a minute, two minutes, five minutes, etc.) to determine various biometric measurements of the user including the average heart rate. In addition, the MCU can collect instantaneous heart rates periodically (e.g., every second, minute, etc.) or the periodic change of the heart rate. Accordingly, the MCU can control the HR sensor to collect a historical recording of biometric data and instantaneous biometric data. The analyzed and raw biometric data can be recorded and transmitted to the paired device, such as a smartphone. In addition, the analyzed and raw biometric data can be uploaded to cloud for storage and further backend analysis for various applications including statistical analysis, customized user data and cumulative data of multiple users.

Figure 4:
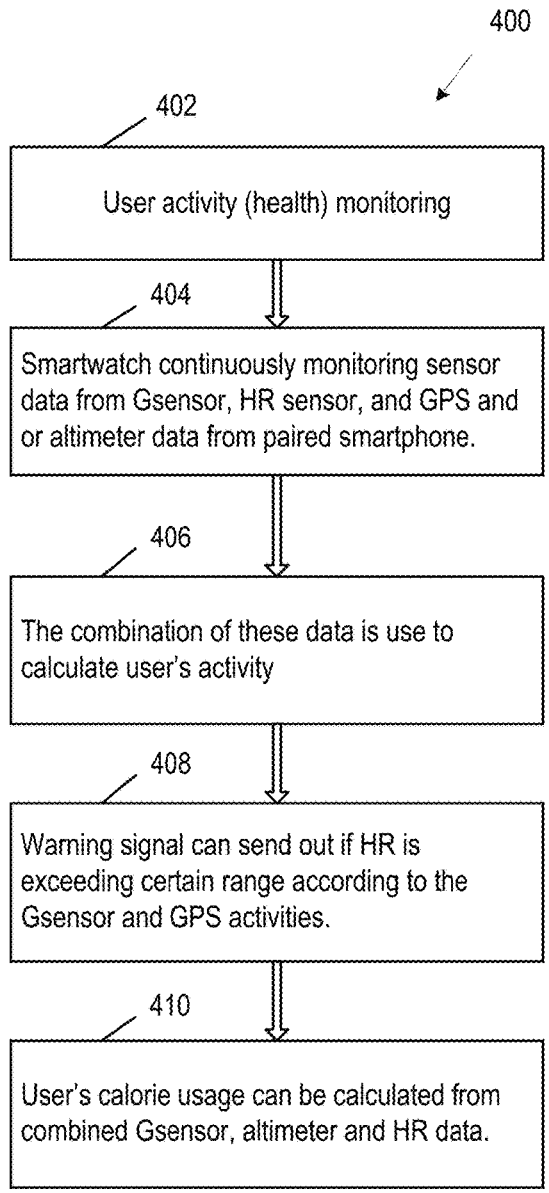
FIG. 4 is a flow diagram showing an exemplary process for health activity monitoring and medically significant event detection.

In some implementations, the raw and analyzed biometric data can be correlated with G sensor data of the watch and GPS data of smartphone to drive the user's physical activities. FIG. 4 is a flow diagram showing an exemplary process 400 for health activity monitoring and medically significant event detection. The process 400 includes performing user activity (e.g., health) monitoring (402). The smartwatch can continuously monitor sensor data from sensors including Gsensor, heartrate sensor, GPS, or altimeter sensor (404). Some of the sensors can be implemented in the host device, such as the smartphone. The combined data from one or more of the sensors can be used to calculate the user's activity (406). The smartwatch can output a warning signal (visual, audio, vibration, etc.) if the sensor data indicates that a biometric measure exceeds a safe threshold (408). For example, a warning signal can be output when the heartrate exceeds a certain range according to the sensors, such as the Gsensor and GPS that monitors the activities of the user. Also, the user's calorie usage (burnt off by activity) can be calculated from combined sensor data from sensors such as the Gsensor, altimeter, or the heart rate sensor (410).

These correlations can be useful to track the user's heart response to different physical activities, and with continuous monitoring, the correlated data can provide useful analysis of the user's health condition and suggest actions to improve it. For example, rather than merely counting or tracking the movement of the user based on motion sensor data alone, biometric data can be correlated with the motion sensor data to determine the intensity of each activity. For example, by correlating the motion sensor data and the biometric data, the MCU can distinguish between walking and running. Also, since the HR sensor can accurately measure the user's heart rate during a particular activity, a more accurate estimate of calories burned during the activity can be determined than merely counting the total number of steps taken by the user. In addition, responsive to the measured biometric data, the MCU can make better suggestions (e.g., run faster, longer, etc.) to achieve a desired goal of burning calories to achieve a certain health condition. Also, the GPS on the smartphone can be used to identify that the user is climbing a hill, on top of a mountain, etc. to further add to the accuracy of the caloric burn and to provide appropriate feedback to the user (e.g., be careful not to run too fast up this hill because it is slippery, too steep, etc.).

Continuous Combined Sensing for Providing Medical Warnings

The motion and biometric sensor data can be combined to identify a medically significant event and to provide appropriate warning or to automatically trigger an appropriate action. For example, the biometric sensor data such as the HR sensor data can be combined with the G sensor data to determine that the user is wearing the smart watch and very little physical activities is detected by the G sensor, but the HR sensor detects that the user's heart rate is increasing quickly to a very high rate. Such combined sensing may indicate a health problem (i.e., medically significant) for the user wearing the watch. When such medically significant event is detected based on the sensor data from a combination of sensors, a warning message may be sent to the user through the display or audio output. In addition, the same warning may be automatically sent to the user's doctor's office, the user's emergency contact, or other appropriate persons. A different person can be assigned to different warnings. Also, the warning message and associated sensor data that triggered the warning message can be sent to an external device, the cloud, hospital medical systems, etc. for further analysis of the sensor data. In some instances, a phone call with a prerecorded message (e.g., name, phone number, address of the user) can be made automatically to an emergency medical response unit (e.g., 911 or fire department).

Continuous Combined Sensing for Correlating with Calendared Events

In some implementations, the raw and analyzed biometric data can be correlated with a user's calendar or schedule data to provide a correlation of user's biometric data such as heart rate with the user's activities. As the user performs the activities on the user's calendar or schedule data, the smart watch will collect biometric data from one or more of the biometric sensors, such as the HR sensor and the BP sensor. After recording the collected biometric data and correlating the collected biometric data with specific event or activity, the MCU can make various determinations and decisions that trigger a mode of operation for the smart phone. The biometric sensor data collection and correlation with specific activities may need to be performed for a predetermined period of time to obtain a statistically significant or otherwise relevant determination and decision.

For example, the HR sensor data can be correlated with the user's calendar or schedule data to determine that a meeting with a difficult person that always elevates the user's heart rate. Based on the correlation result, the MCU can send a notification warning to the user that a potentially difficult meeting is coming up soon on the calendar. The notification can also include suggestions on how to prevent the predicted heart elevation. Such suggestions can include suggesting to play a song, display a picture, play a video, etc. of some content that has been correlated to the user's heart rate being reduced (i.e., has a calming effect on the user). Also, the MCU can suggest certain food that may calm the user. The MCU can also select a different driving route to the meeting that will be less stressful or suggest that the user leave early to avoid added stress.

Other biometric sensor data such as from the BP sensor can also be correlated with the user's calendar or schedule data. In a manner similar to the HR sensor data correlation with user's calendar or schedule data, the BP sensor data correlation can inform the user of specific activity or even that triggers a higher blood pressure for example.

After correlation analysis has been completed to correlate biometric sensor data with user's activities or events, the MCU can categorize and rank the activities or events based on the correlated biometric sensor data. Examples of categories of events or activities include: (A) Elevated Heart Rate Events (stressful or excited), (B) Low Heart Rate Events (calming), and (C) Normal Heart Rate Events (uneventful or boring). In addition, within each category, each event can be ranked to identify the various levels of each category (e.g., most exciting to least exciting events within the Elevated Heart Rate Events). Similar categorization and ranking can be performed for other biometric sensor data, such as BP sensor data.

Figure 5:
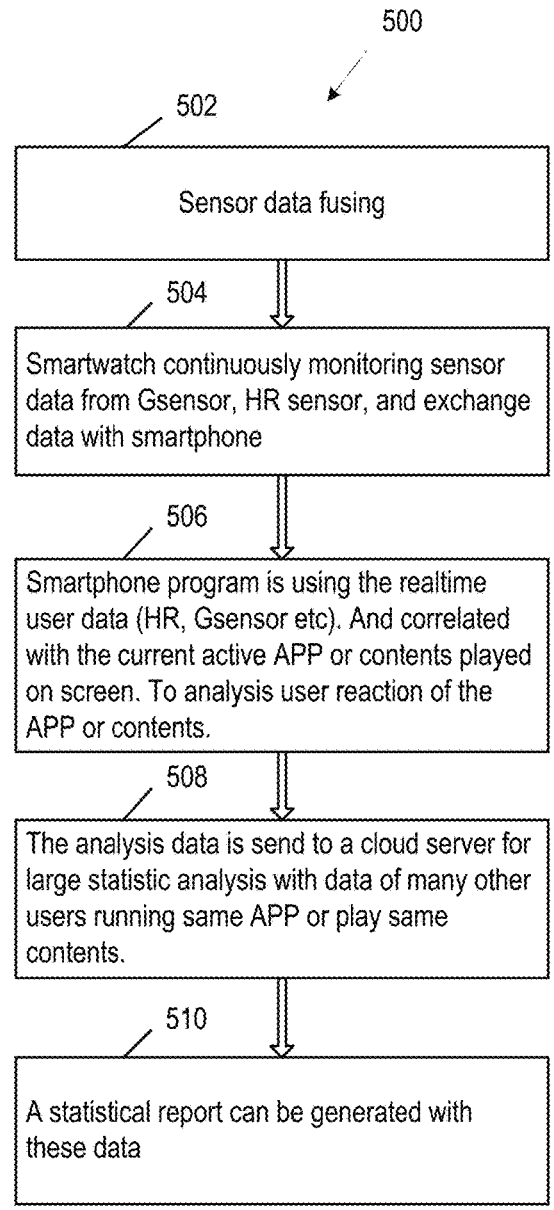
FIG. 5 is a flow diagram showing an exemplary process for fusing or correlating sensor data with activities performed on a paired device, application and content.

Continuous Combined Sensing for Correlating with Paired Device Activities/Events FIG. 5 is a flow diagram showing an exemplary process 500 for fusing or correlating sensor data with activities performed on a paired device, application and content. The process 500 includes sensor data fusing (502). Smartwatch can continuously monitor the sensor data from one or more of the sensors such as the Gsensor, HR sensor, etc. and exchange date with the host device, such as the smartphone (504). The smartphone can use the real-time user data such as the heartrate, Gsensor, etc. and correlate the data with the current active application or contents played on the screen to analyze user reaction to the application or contents (506). The analysis data (of the user reaction to the application or contents) can be sent to a cloud server for more backend analysis (508). For example, the cloud server can perform larger statistical analysis with data from many other users running the same application or playing the same content. A statistical report can be generated with the data from the clouds (510).

In some implementations, the collected sensor data can be analyzed to correlate with activities or events of the paired device such as smartphone activities. Thus, the MCU can control the motion and biometric sensors to collect sensor data while various activities, events or operations are being performed on the paired device, such as the smartphone. Using the RTC on the smart phone, the MCU can sync with the time on the paired device for accurate syncing of the collected sensor data with the events and activities on the paired device. For example, while the smartphone's call function is actively performing a voice call connection with a device associated with a certain phone number, the HR sensor may sense that the user's heart rate is higher or lower than the user's normal heart rate. Then the MCU may make a determination that the telephone number correlates with an elevated heart rate. Also, while the smartphone's media player is playing certainly music or video, the HR sensor senses that the user's heart rate is lower or higher than user's normal heart rate. Similarly, while the smartphone's web browser may be actively displaying certain web content or running certain application, the HR sensor senses that the user's heart rate is different from the user's normal heart rate. These correlated analysis and result can provide the user with useful health-related feedback information to identify the activities or events that tend to change the user's biometric measurements such as the heart rate and blood pressure. In addition, the correlation data can further provide the categories of different biometric effects (e.g., identification of heart rate elevating events and heart rate reducing events, etc.) and rankings within each category as described above.

Continuous Combined Sensing for Targeted Sensor-Based Services and User Feedback In some implementations, the correlated information as described in this document can be collected by content providers through an application (e.g., an web APP), for example, to provide targeted feedback to the user based on the user's reaction (inferred from biometric data) while using the APP or consuming contents. These correlation data between the user's biometric sensor data and the APP or content or even a particular portion of the content can be extreme useful for the APP or content provider.

To perform correlation between the biometric sensor data and a particular APP or content, an APP can use a special application programming interface (API) to link to the smart watch data (e.g., HR data), other sensor data or analysis data. Thus, the APP or content provider can determine the exact biometric reaction (based on HR sensor data, for example) to a particular APP or content to determine whether the user enjoyed the APP, was excited to consume the content, etc. Thus, the content or APP provider can receive instant feedback from each user specific to that user's biometric sensor data.

By correlating a user's biometric sensor data with a particular APP or content, the APP or content provider can obtain information beyond the simple fact of whether the user used or consumed the content. Rather, another layer of user feedback (biometric feedback) can be added to determine whether the user was excited (e.g., heart rate elevated) or bored (e.g., heart rate normal) or calmed (e.g., heart rate reduced) when the user used the APP or consumed the content. Thus, the APP or content provider can not only know whether the user used the APP or consumed the content, but also know how the user reacted to the APP or content. Moreover, because the biometric sensor data is not likely to be manipulated or faked by the user, the information obtain is more accurate to discern whether the user really enjoyed the APP or the content, for example.

Continuous Combined Sensing for Identifying Context of User Activity

The motion and biometric sensor data can be analyzed to determine the context of the user's activity and the biometric reaction of the user to that activity within the identified context. For example, motion and biometric sensor data correlated to the paired smartphone can be used to determine that a user like to listen to a particular piece of music while running. This determination is possible by using the motion sensors such as the G sensor and the altimeter sensor that the user is running. The biometric sensor, such as the HR sensor can confirm that the user is running because the heart rate is elevated with the G sensor and the altimeter sense motion associated with running. Moreover, a correlation with the user's smartphone may further confirm that the user has scheduled a run through a local part at the exact time that the motion and biometric sensors predicted a running activity. In this manner of sensor data correlation with paired device, the MCU can determine the most listened music while the user is running, walking, sitting down, at office, at home, etc. Other similar determination can be made.

In a similar manner, a provider of an APP or content can determine (e.g., through the motion sensors) that a particular user tends to stand up, sit down, pace back and forth, lie down, etc. when using the APP or consuming the content. Thus, the provider of the APP or content can obtain even obtain the posture of the user's body when the user uses the APP or consumes the content. Then the provider of the APP or content can provide targeted service (advertisement, coupon, offers, etc.) associated or appropriate with the determined posture. Moreover, the provider of the APP or content can configure the APP or content to customize the APP or content experience for the correlated body posture of the user.

Continuous Combined Sensing for Crowd Sourcing and Cloud Services

Figure 6:
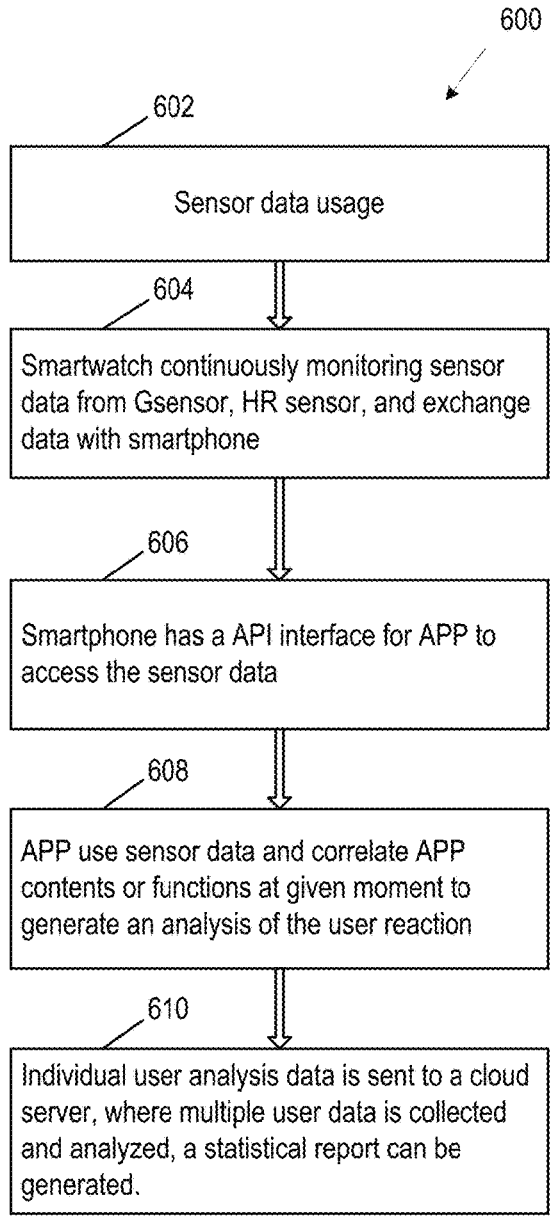
FIGS. 6 and 7 are flow diagrams showing exemplary processes for correlating sensor data with activities on a paired device and reporting the collected and correlated data to a cloud server for crowd sourcing.
Figure 7:
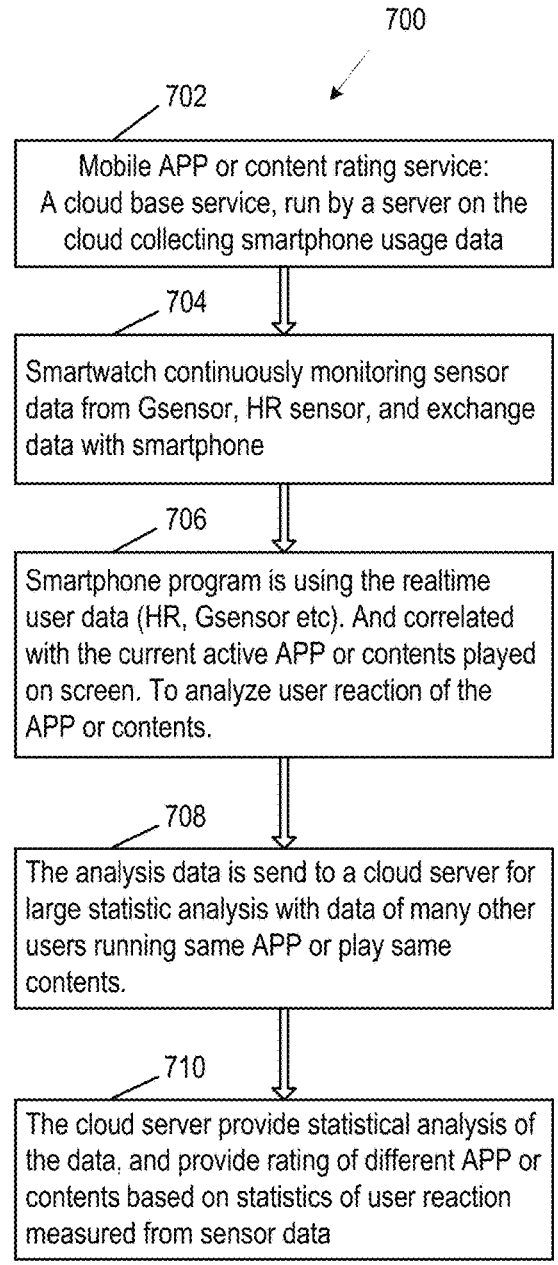

FIGS. 6 and 7 are flow diagrams showing exemplary processes 600 and 700 for correlating sensor data with activities on a paired device and reporting the collected and correlated data to a cloud server for crowd sourcing. Process 600 includes processing sensor data usage (602). The smartwatch can continuously monitoring sensor data from Gsensor, HR sensor, etc. and exchange data with smartphone (604). Smartphone can have an API interface for a given application to access the sensor data (606). The application can use the sensor data and correlate APP contents or functions at a given moment to generate an analysis of the user reaction (608). Individual user analysis data is sent to a cloud server, where multiple user data is collected and analyzed, and a statistical report can be generated (610).

Process 700 includes operating a Mobile APP or content rating service, such as a cloud base service run by a server on the cloud collecting smartphone usage data (702). The smartwatch can continuously monitoring sensor data from Gsensor, HR sensor, etc. and exchange data with smartphone (704). The smartphone program can use the real-time user data (HR, Gsensor etc.) and correlated with the current active APP or contents played on screen to analyze user reaction of the APP or contents (706). The analysis data is send to a cloud server for larger statistical analysis with data of many other users running same APP or play same contents (708). The cloud server can provide statistical analysis of the data, and provide rating of different APP or contents based on statistics of user reaction measured from sensor data (710).

In some implementations, the MCU can transmit the motion and biometric sensor data from each consenting user automatically to a centralized cloud based service system to collect the motion and biometric sensor data related correlation analysis. Software utilized an API running on the smart watch or paired smartphone can collect the sensor data and the correlated user activity on the smartphone can be collected by the service to provide statistics of the smartphone or watch response to certain application or content. The service can collect similar sensor data and correlation analysis data from multiple users to obtain a crowd sourced statistics on the user of a particular application or content. For example, the compiled sensor data and correlation analysis data from multiple users can be used to create a rating system of media content (e.g., music) most likely to slow down a user's heart rate. Thus, a user wanting to listen to a calming or relaxing music can use the service to identify and purchase/rent the desired music to relax the user. Similarly, the user can identify the desired music that is most ideal for running, doing homework, eating, flying, driving, taking a nap, doing a particular chore, etc. Because the ratings are based on the motion and biometric data collected while the user is performing a particular activity or using a particular application or consuming a particular content, the resulting ratings system more accurately reflects the reactions of the user. Moreover, the user does not need to manually indicate whether the user liked or disliked a piece of music, which is more convenient for the user and more accurate (i.e., difficult to fake the biometric data).

While this document contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this document.

What is claimed is:

1. A smart watch comprising:
   at least one motion sensor to sense motion of a user and generate motion data from the sensed motion;
   at least one biometric sensor to sense one or more biometric parameters of the user and generate biometric data from the sensed one or more biometric parameters, wherein the one or more biometric sensors include a heartbeat sensor;
   an optical sensor to generate optical data of the user containing information indicative of whether the user is maintaining an eye-focus on the smart watch;
   a microcontroller to control the at least one motion sensor, the at least one biometric sensor, and the optical sensor;
   a real-time clock to maintain time;
   a wireless radio to pair with an external device; and
   a display module,
   wherein the microcontroller is configured to:
      analyze the motion data and the biometric data to switch between a standard mode and an active mode,
      analyze the optical data to determine whether the user is maintaining an eye-focus on the smart watch, wherein the smart watch is kept in a current mode or switched to a standby mode in response to whether the user is maintaining the eye-focus on the smart watch,
      pair with the external device comprising a smart phone,
      correlate the biometric data and the motion data with a current application running on the smart phone or content being played to determine a reaction of the user to the current application or content,
      process the motion data and the biometric data to identify an activity being performed by the user, wherein the identified activity comprises running, swimming, or walking, and
      couple the biometric data with the motion data to determine whether the identified activity burns more calories than other activities,
   wherein the smart watch is configured to continuously monitor, after an authentication of the user, the heart beat sensor to determine whether the smart watch is being continuously worn by the user, and configured so that when the smart watch is continuously worn by the user, continuing the authentication of the user and discontinuing the authentication when the smart watch is taken off the user.

2. The smart watch of claim 1, wherein the two or more of the at least one motion sensor comprises a 3-D accelerometer and the at least one biometric sensor includes a heart rate sensor, and wherein the microcontroller is configured to:
   determine an extent of the user's motions, and an intensity of the user's motions based on a combined sensor data from the two or more of the at least one motion sensor and the at least one biometric sensor.

3. The smart watch of claim 2, wherein the identified activity is a form of exercise, and wherein the microcontroller is configured to analyze sensor data from the heart rate sensor to estimate total calories burned during the activity.

4. The smart watch of claim 2, wherein the microcontroller is configured to identify a medically significant event based on the combined sensor data from the 3-D accelerometer and the heart rate sensor.

5. The smart watch of claim 2, wherein the wireless radio comprises a Bluetooth low energy (BLE) radio.

6. The smart watch of claim 5, wherein the microcontroller is configured to sync time with the paired smart phone.

7. The smart watch of claim 5, wherein the BLE radio is configured to pair with the external device comprising the smart phone, and wherein the microcontroller is configured to correlate sensor data from two or more of the at least one motion sensor and the at least one biometric sensor with the activity.

8. The smart watch of claim 7, comprising:
   memory for storing an application program interface (API), wherein the API is configured to collect sensor data from two or more of the at least one motion sensor and biometric sensor during the activity and transmit the collected data to a cloud server.

9. The smart watch of claim 1, wherein the at least one motion sensor and the at least one biometric sensor are configured to continuously collect sensor data.

10. The smart watch of claim 1, comprising one or more touch sensors for receiving user input.

11. The smart watch of claim 10, wherein the one or more touch sensors are integrated into the display module.

12. The smart watch of claim 10, wherein the one or more touch sensors are located at one or more surfaces separate from the display module.

13. The smart watch of claim 12, wherein the one or more surfaces separate from the display module include a surface around or next to the display module.

14. The smart watch of claim 12, wherein the one or more surfaces separate from the display module include a surface of a wrist band.

15. The smart watch of claim 1, wherein the display module includes a display device selected from the following: an organic light emitting diode (OLED) display, an E-ink display, a liquid crystal display (LCD), and a simply multiple LED display.

16. The smart watch of claim 1, wherein the display module is configured to display text and graphic information.

17. The smart watch of claim 1, comprising:
   a data storage device configured to operate in concert with the microcontroller to store sensor data from the one or more motion or the one or more biometric sensors when operating independent of, and not in communication with, an external device.

18. The smart watch of claim 17, wherein the microcontroller and the wireless radio in combination are configured to transfer sensor data to the external device or to a cloud server when the smart watch is within a wireless communication range with the external device.

19. The smart watch of claim 1, comprising:
a fingerprint sensor configured to perform the authentication of the user as a valid user of the smart watch.

20. The smart watch of claim 19, wherein the fingerprint sensor is configured to perform the authentication by comparing a sensed fingerprint data with a stored fingerprint profile of the valid user of the smart watch.

21. The smart watch of claim 1, wherein the multiple modes include at least:
the standard mode wherein the microcontroller displays on the display module a time and the one or more motion sensors and the one or more biometric sensors generate data in the background, and
the active mode wherein the microcontroller displays on the display module newly generated data and audio or vibration notification signals are enabled.

22. A method performed by a smart watch comprising:
sensing at least one motion data;
sensing at least one biometric data including a heartbeat;
sensing at least one optical data of the user containing information indicative of whether the user is maintaining an eye-focus on the smart watch;
analyzing, by a controller, the at least one motion data and the at least one biometric data;
analyzing the optical data to determine whether the user is maintaining the eye-focus on the smart watch;
responsive to the analyzing the at least one motion data and analyzing the at least one biometric data, and the optical data, switching between a standard mode and an active mode of the smart watch, wherein the smart watch is kept in a current mode or switched to a standby mode in response to the optical data including the confirmation that the user is maintaining the eye-focus on the smart watch;
correlating the at least one motion data and the at least one biometric data with a current application running on an external device or content being played on the external device to determine a reaction of the user to the current application or content;
processing the motion data and the biometric data to identify a current activity performed by the user, an extent of the user's motions, and an intensity of the user's motions based on a combined sensor data from the at least one motion data and the at least one biometric data, wherein the current activity comprises running, swimming, or walking; and
coupling the at least one biometric data with the at least one motion data to determine whether the current activity burns more calories than other activities,
wherein the smart watch is configured to, after an authentication of the user, continuously monitor the heart beat to determine whether the smart watch is being continuously worn by a user, and when smart watch is continuously worn by the user, continuing the authentication of the user and discontinuing the authentication when the smart watch is taken off the user.

23. The method of claim 22, wherein the processing the motion data and the biometric data determines a total calories burned during the current activity.

24. The method of claim 22, further comprising:
correlating the at least one motion data and the at least one biometric data to the current activity.

25. The method of claim 22, comprising:
pairing with the external device comprising a smart phone.

26. The method of claim 22, wherein the at least one biometric sensor includes a blood pressure sensor.

* * * * *